United States Patent [19]
Gartside et al.

[11] Patent Number: 5,254,788
[45] Date of Patent: Oct. 19, 1993

[54] PROCESS FOR THE PRODUCTION OF OLEFINS FROM LIGHT PARAFFINS

[75] Inventors: Robert J. Gartside, Summit, N.J.; Axel R. Johnson, N. Babylon, N.Y.

[73] Assignee: Stone and Webster Engineering Corporation, Boston, Mass.

[21] Appl. No.: 757,177

[22] Filed: Sep. 10, 1991

[51] Int. Cl.$^5$ .................. C07C 5/333; C07C 5/327
[52] U.S. Cl. .................................. 585/659; 585/654; 585/660; 585/661
[58] Field of Search ............... 585/659, 654, 660, 661

[56] References Cited

U.S. PATENT DOCUMENTS

| Re. 33,728 | 10/1991 | Dean et al. | 208/120 |
|---|---|---|---|
| 2,335,488 | 11/1943 | Conrad | 585/659 |
| 3,674,887 | 7/1972 | Clay | 585/621 |
| 4,108,913 | 8/1978 | Spoerke et al. | 585/663 |
| 4,287,375 | 9/1981 | Möller et al. | 585/440 |
| 4,376,225 | 3/1983 | Vora | 585/659 |
| 4,433,984 | 2/1984 | Gartside et al. | 55/196 |
| 4,453,865 | 6/1984 | Norton | 406/24 |
| 4,459,071 | 7/1984 | Norton et al. | 406/108 |
| 4,615,792 | 10/1986 | Greenwood | 585/659 |
| 4,762,961 | 8/1988 | Guttmann et al. | 585/661 |
| 4,814,067 | 3/1989 | Gartside et al. | 208/127 |
| 4,919,898 | 4/1990 | Gartside et al. | 422/219 |
| 4,956,510 | 9/1990 | Harandi | 585/419 |

FOREIGN PATENT DOCUMENTS 0315179  5/1989  European Pat. Off.

OTHER PUBLICATIONS

Masterton & Slowinski, *Chemical Principles*, Philadelphia; W. B. Saunders Co. (4th ed. 1977) pp. 154–155.
S. H. Hobbs et al., "Propylene and Butenes By Selective Dehydrogenation", Presented at the ACS National Meeting, Washington D.C., Aug. 29, 1990, pp. 1–29.
F. M. Ashmawy, "Kinetic Investigations of the Reaction of Propane with Sulphur Dioxide on a Palladium-Alumina Catalyst", J. Chem. Tech. Biotechnol. 1984, 34A, 183–186.
F. M. Ashmawy et al, "Active Phases in Chromia-Alumina Dehydrogenation Catalysts", J. Chem. Soc., Faraday Trans. 1, 1984, 80, 1985–1990.
J. N. Miale et al., "Catalysis by Crystalline Aluminosilicates", Journal of Catalysis, 6, 278–287 (1966).
P. S. Van Damme et al., "Thermal Cracking of Propane and Propane-Propylene Mixtures: Pilot Plant Versus Industrial Data", AIChe Journal, vol. 21, No. 6, Nov. 1975, pp. 1065–1073.

*Primary Examiner*—Anthony McFarlane
*Assistant Examiner*—Nhat Phan
*Attorney, Agent, or Firm*—Hedman, Gibson & Costigan

[57] ABSTRACT

The present invention relates to a process for the production of olefins from light paraffins. Specifically, the present invention relates to a process for the production of olefins from ethane, propane, butane, isobutane, pentane and isopentane, preferably utilizing moderate or high activity dehydrogenation catalysts at kinetic residence times of from about 0.1 to about 2.0 seconds, and at temperatures of from about 900° F. to about 1600° F. The present invention further relates to the production of an olefin from its corresponding paraffin, and a process for the production of a mixture of olefins.

39 Claims, 6 Drawing Sheets

PROCESS FOR THE PRODUCTION OF OLEFINS FROM LIGHT PARAFFINS

FIELD OF THE INVENTION

This invention relates to a process for the production of olefins from light paraffins.

BACKGROUND OF THE INVENTION

The dehydrogenation of light hydrocarbons can be performed several ways. In the following, the dehydrogenation of propane will be examined, however, the principles described herein apply equally to the dehydrogenation of other light hydrocarbons. Light hydrocarbons are defined as having five carbon atoms or less, i.e., ethane, propane, butane, isobutane, pentane and isopentane.

It is known in the art to dehydrogenate propane to propylene such as by endothermic vapor phase dehydrogenation. The dehydrogenation can occur either thermally or catalytically. Simultaneously, other thermal reactions occur which crack and/or degrade the propane molecule and produce compounds smaller than propylene. Also, propylene itself is subject to unwanted thermal degradation reactions.

The principal reactions in propane dehydrogenation include the following:

$$C_3H_8 \xrightarrow{\text{catalyst and heat}} C_3H_6 + H_2 \quad \text{catalytic dehydrogenation}$$

$$C_3H_8 \xrightarrow{\text{heat}} C_3H_6 + H_2 \quad \text{thermal dehydrogenation}$$

$$C_3H_8 \xrightarrow{\text{heat}} C_2H_4 + CH_4 \quad \text{thermal cracking}$$

$$2C_3H_6 \xrightarrow{\text{heat}} C_4H_6 + C_2H_4 + H_2 \quad \text{thermal degradation}$$

All of these reactions require substantial quantities of heat per pound of feed.

Propylene is produced commercially by the thermal cracking of propane in pyrolysis coil cracking reactors, along with substantial quantities of ethylene and methane; by the catalytic dehydrogenation of propane; and by the recovery of co-produced propylene from the effluent when cracking heavier compounds either thermally or catalytically. Catalytic dehydrogenation typically occurs in fixed bed reactors where propane is passed over a catalyst bed and reaction occurs.

The choice of process depends upon the selectivity and/or the conversion of propane to propylene desired. Thermal cracking reactions are not selective to propylene and the process yields substantial quantities of co-produced ethylene and methane. Thermal cracking can however achieve complete conversion of the feedstock thus eliminating recycle of the feedstock.

If propylene selectivity is desired, i.e., higher yields of propylene per unit propane feed, catalytic dehydrogenation is preferred. The catalysts allow the dehydrogenation reaction to occur at substantially lower temperatures than required for thermal dehydrogenation. The lower temperatures suppress unwanted thermal cracking reactions and high yields of propylene per unit propane are obtained. At these lower temperatures, however, absolute conversion is limited by equilibrium. Thus, while selectivity to propylene is high, conversion is low. Such a process thus requires substantial recycle of unreacted feed.

Several commercial processes exist for catalytically dehydrogenating hydrocarbons using fixed bed technologies. Such processes are carried out either adiabatically or isothermally.

There are two major commercial processes using adiabatic conversion over a catalyst. In one of the processes, the heat for the endothermic dehydrogenation reaction is provided by preheating the reactor feed to temperatures greater than the reactor outlet. The propane feed is highly diluted with an inert diluent (steam or hydrogen/methane). This diluent acts primarily as a heat carrier but also serves to minimize catalyst fouling. Catalyst is gradually removed from the bed, regenerated, and returned. The rate of circulation is quite low; bed turnover is measured in days and is not a source of heat. This "moving bed" operation is quite complex mechanically and limited to very low circulations.

Since the dehydrogenation reaction requires substantial quantities of heat per unit propane, failure to dilute the mix would require the propane to be preheated to a very high temperature, causing extensive thermal reactions prior to entering the catalyst bed. This would result in a system with poor selectivity to propylene. To compensate, the flow of diluent is typically equal to or greater than the flow of feed. High diluent flows reduce the capacity of the processing equipment.

The dehydrogenation is normally carried out in two or three stages. The partially reacted feed mixture is reheated in each stage to provide the heat necessary to complete the reaction. Interstage temperatures of between 565° C. and 630° C. are necessary to obtain commercially acceptable conversion levels and to minimize thermal cracking of the feed.

Even with high dilution levels, equilibrium limits the reaction to only about 40% conversion per pass at temperatures required for high selectivity. This requires that the unreacted material be recycled if the goal is to completely convert the fresh feed. At 40% conversion per pass, 1.5 lb of recycle is fed to the reactor for every 1.0 lb of fresh feed. Low conversion and high dilution represent an inefficient use of equipment capacity since effectively only 40% of the reactor is used without even considering the dilution. With a one to one molar dilution rate, only 20% of the potential reactor capacity for fresh feed is used. Furthermore, the high recycle rates and high dilution require extensive downstream separation equipment.

Another adiabatic conversion process passes the feed mixture over a highly preheated fixed catalyst bed. As the reaction proceeds, the catalyst gradually gives up its heat to reaction and cools, leading to changes in conversion over time. Eventually (time measured in minutes), the extent of conversion becomes too low for reasons of control and the reactor is taken off line. A second reactor, which was being preheated by direct contact with hot combustion gases while off-line, is then switched on-stream. A continuous process is achieved by the cycling of several reactors simultaneously. This involves complicated valving and control systems. Conversions in this process are slightly higher (on average 60%) than the previous process but the process still requires substantial recycle. Further, conversions change with time and products of combustion (from the reheat cycle) contaminate the product gas flow.

In a non-adiabatic commercial process the catalytic dehydrogenation of hydrocarbons is carried out in a gas fired tubular reactor. Conversions of only about 40 mole percent are generally achieved in such reactors. In addition, this process requires the recirculation of large quantities of hot gas thereby consuming substantial amounts of energy. Also, many tubes are required to achieve high capacities in this process.

Another non-adiabatic process involves the catalytic fixed bed dehydrogenation of hydrocarbons in a nearly isothermal fixed bed reactor. (See, e.g., U.S. Pat. No. 4,287,375, Moller, et al.) The tubular reactor is immersed in an isothermal molten salt bath maintained at a temperature of 600° C. while the reaction temperature is about 20° C. less than the molten salt bath. In this process, a water vapor/ethylbenzene mixture at a ratio of about 1.2-1.5 kg steam/1.0 kg hydrocarbon is introduced into the dehydrogenation reactor. High dilution levels result in low feedstock capacity.

Both of these non-adiabatic processes suffer from difficulties in providing heat to the fixed bed of catalysts. One method of adding heat is to preheat the feed and/or diluent as mentioned above. This technique has a negative effect on reactor capacity and selectivity. The second method is to divide the bed into a plurality of smaller beds, i.e. tubes, and allow heat to flow through the walls of the tubes. This requires complex mechanical systems, but has been achieved as referenced above.

It is even more difficult to achieve short kinetic residence times in these fixed bed systems. As gas flows over a bed of catalyst, pressure is lost. In order to avoid large unfavorable pressure drops, the gas velocity must be low and catalyst particle sizes must be large. With low gas velocity, the fixed bed must be shallow yet have considerable cross-sectional area to retain high capacity. This leads to distribution problems not only for feed input into the catalyst bed but for distribution of product cooling media to stop the unwanted thermal side reactions from continuing once the product has left the catalyst bed. For the tubular reactors mentioned above, distribution is especially critical. Also, the large catalyst particles required for low pressure drop create significant diffusional resistances to reaction which precludes operation at short residence times.

There is a further consideration of residence time since all reactions continue until either the feedstock is exhausted or the process operating conditions have changed. Catalytic reactions are usually stopped by having the product gas exit the catalyst bed, however, this does not stop the thermal reactions. Heat must be removed from the system or a quench medium added to the product gas in order to reduce the temperature and stop the thermal reaction. Fixed bed systems, with either their plurality of tubes or high cross-sectional area, are not well suited for rapid heat removal or rapid introduction of a quench medium to cool the product gasses and prevent further reaction.

Low kinetic residence times are therefore difficult to achieve in conventional dehydrogenation reaction systems and, as such, these systems cannot reach a favored reaction temperature without a loss of selectivity. These conventional systems also have limitations involving heat input, feed distribution and pressure drop regardless of the feed.

It would therefore represent a notable advance in the state of the art if a dehydrogenation process could be provided which operates at high temperature, short kinetic residence time, low pressure drop, low feed dilution levels, high conversion and high selectivity, and which can facilitate catalyst regeneration.

SUMMARY OF THE INVENTION

It is therefore an object of the present invention to provide a process for producing high yields of corresponding olefins from paraffins of five carbon atoms or less at a high per-pass rate of conversion. It is yet another object of the present invention to achieve high selectivity and greater capacity per unit reactor. It is a further object to produce olefins from paraffins of five carbons or less without employing extensive feed preheating, high dilution levels, reheating of feed product at intermediate stages and/or high pressure drops, and to further provide a process which facilitates continuous catalyst regeneration.

A still further object of the invention is to provide a process for dehydrogenating paraffins having five or fewer carbon atoms that can either operate at higher temperatures, short kinetic residence times, and with moderate activity catalysts, or can operate at lower temperatures, short kinetic residence time, and with higher activity catalysts while still achieving high conversion per pass of the feed hydrocarbon.

It is also an object of the present invention to provide a process for dehydrogenating paraffins having sufficient heat input capability to allow for high conversion and simultaneous thermal cracking to achieve mixed thermal and catalytic yields.

These and other objects are realized by a process for producing olefins from paraffins having five or fewer carbon atoms, said process comprising:
(a) introducing a dehydrogenation catalyst to the top of a tubular downflow reactor to produce a catalyst stream;
(b) introducing a feed stream comprising a paraffin having five or fewer carbon atoms into the catalyst stream at a feed introduction point;
(c) mixing the catalyst stream and the feed stream in a mixing zone to produce a mixed stream;
(d) passing the mixed stream downwardly through a reaction zone at a temperature of from about 900° F. to about 1600° F. and a pressure of from about 10 to about 100 psig to produce an effluent comprising olefins; and
(e) passing the effluent comprising olefins through a separator to separate the catalyst from the effluent, thereby producing a separated catalyst stream and a clean effluent stream;
wherein the kinetic residence time of the process is from about 0.1 to about 2.0 seconds.

The preferred paraffins are selected from the group consisting of ethane, propane, isopropane, butane, isobutane, pentane, and isopentane. The feed may optionally contain minor amounts of .other paraffins. It is also contemplated to add a diluent to the feed, which may be any suitable compound which is inert in the reaction, such as steam, hydrogen, methane, and the like.

The catalyst solids comprise an inert carrier such as amorphous or kaolin clay or alumina impregnated with one or more catalytically active ingredients. It is known to those skilled in the art that certain metals and their oxides act as catalysts for the dehydrogenation of paraffins. Primarily, these metals are from the noble metal group or the transition metal group as defined by the periodic table of elements. Examples of noble metals include iron (Fe), nickel (Ni), palladium (Pd), and platinum (Pt). Examples of transition metals include vanadium (V), chromium (Cr), and manganese (Mn). It is also known in the field that certain alkali compounds, such as potassium oxide ($K_2O$), are beneficial in promoting the activity of the metal oxides as catalysts. Further, other elements such as tin (Sn), and lead (Pb), have exhibited catalytic activity in their oxide form. The catalyst may further comprise an aluminosilicate zeolite.

In preferred embodiments, the process further comprises the steps of quenching the effluent stream and/or regenerating and reheating the catalyst and then returning the catalyst to the top of the reactor.

In another preferred embodiment, the catalyst of step (a) is delivered to the reactor at a temperature of from about 1300° F. to about 1800° F., and the weight ratio of catalyst to feed in the mixed stream of step (c) is from about 5 to about 100. The catalyst of step (a) may optionally be accelerated prior to the feed introduction point. The feed may also be introduced directly into the mixing zone.

In especially preferred embodiments, the catalyst comprises particles of from about 20 to about 500 microns in diameter, which have a surface area of from about 20 to about 450 $m^2/g$.

In another preferred embodiment, the process does not utilize indirect heating means.

In further embodiments, olefins are produced from corresponding paraffins at temperatures of from about 900° F. to about 1300° F. and a residence time of from about 0.1 to about 0.5 seconds. In yet further embodiments, a mixture of olefins is produced at a temperature of from about 1300° F. to about 1600° F. at a residence time of from about 0.25 to about 2.0 seconds, and the mixture of olefins has an outlet yield ratio of from about 0.5 to 1.0.

DETAILED DESCRIPTION OF THE PRESENT INVENTION

The present invention may be operated employing conventional dehydrogenation catalyst, moderate activity dehydrogenation catalyst and/or high activity dehydrogenation catalyst.

The term "catalytic activity," as used throughout this application, refers to the rate of reaction occurring in the presence of a catalyst compared to the rate of the same reaction occurring without the catalyst. It is a relative term that must be defined with reference not only to the specific reaction (e.g., dehydrogenation) but to a number of other parameters including the catalytically active ingredients, their specific form (e.g., crystalline structure), the presence or absence of any promoters, the amount of catalyst present, the carrier, its structure (e.g., pore size, surface area, etc.), and the operating conditions including not only temperature and pressure, but also other reactants, diluents, or "poisons." There are, for example, cracking catalysts, reforming catalysts, synthesis catalysts, as well as dehydrogenation catalysts; all named by their ability to promote (increase the rate of) a specific chemical reaction. In many references, however, catalytic activity is used synonymously with reaction rate and definitions are thus even more critical.

The terms "high activity", "moderate activity" and "low activity" are also relative and must be defined against a reference. A specific catalyst could exhibit high activity in one particular environment and at low temperature while exhibiting low activity in a different environment and at a high temperature.

The process of the subject invention is directed to processes operating at short kinetic residence times and high temperatures. This allows operation in more favorable equilibrium conditions without the excessive thermal degradation that would occur if higher temperatures were used with conventional kinetic residence times. The process operates with a dilute flowing catalyst system where the flowing catalyst density is considerably less than that of a packed or fixed bed. The amount of catalyst is thus a function of the catalyst to feed ratio (a variable).

Commercial fixed bed dehydrogenation reaction systems operate at temperatures that average near 650° C. Further, in a fixed bed, the catalyst is in a packed form at its maximum density with respect to the gas (maximum sq meters of catalyst surface per unit volume). Since the rate of reaction is a function of both the activity of the catalyst and of the quantity of catalyst present, the process of the subject invention preferably employs a higher catalyst activity than that for a fixed bed, all else being equal, to produce an equivalent yield.

This is best demonstrated by example. At a temperature of 650° C. and the solid density of a packed bed, the ratio of the rate of catalytic dehydrogenation to the summation of the rates of the rate of thermal dehydrogenation and thermal cracking of propane is 3.0. In other words, in commercial dehydrogenation systems operating under their preferred conditions, the rate of catalytic reaction is three times the rate of thermal reaction. This ratio produces high yield selectivity. This same ratio is achieved for the subject process operated at the same temperature (650° C.) and its normal process solid flow (lower flowing density) when the rate constant for catalytic dehydrogenation is approximately 20 times greater than that presented above. The higher rate of catalytic reaction is required to compensate for the lower catalyst density.

As the temperature is increased to achieve a more favorable equilibrium, the rates of the thermal reactions increase more rapidly than do the rates of the catalytic reactions. For the fixed bed at a temperature of 750° C. using commercial catlaysts, the thermal reactions predominate and the rate of catalytic dehydrogenation is 60% of the sum of the rates of the thermal reactions. At this temperature level, the rate constant for the catalytic dehydrogenation reaction to be used in the subject process must be 100 times larger than that for the commercial fixed bed catalyst (also at 750° C.) to achieve the current commercial ratio of catalytic rate to thermal rates (i.e., a ratio of 3.0).

For the purpose of this discussion, a catalyst is considered to have a "high activity" if the catalytic dehydrogenation rate constant is greater than a factor of 300 times higher than that of the commercial catalyst at the same temperature. A catalyst is considered to have a "moderate" activity if the catalyst dehydrogenation rate constant is between a factor of 50 and 300 times higher than that of the commercial catalyst at the same temperature. Thus operation of the process of the present invention with high activity catalyst at its lower catalyst densities will result in a higher ratio of catalytic to thermal reactions than existing commercial systems when operated at conventional temperatures (i.e., approximately 650° C.). Further, it will result in a similar ratio (3.0) at very high temperatures (above 750° C.). Operation of the process with a moderate activity catalyst will give high catalytic to thermal reaction rate ratios at conventional temperatures (650° C.) and similar ratios at higher temperatures (750° C.).

In the practice of the present invention, the hot catalyst solids are accelerated into the top of the reactor using either a diluent, such as those listed above, or a portion of the feed of mixed paraffin and diluent.

The feed and catalyst solids are rapidly mixed and the combined stream of solid catalyst, paraffin, diluent and optional accelerator is passed down through the reactor where the hydrocarbon undergoes thermal and catalytic reactions including dehydrogenation. The operating conditions of the reactor are generally from about 900° F. to about 1600° F. at a pressure of from about 10 psig to about 100 psig with a hydrocarbon residence time from the point of feed introduction to the point of product quench of from about 0.1 seconds to about 2.0 seconds.

Kinetic residence time is defined as the time during which any significant reaction is taking place; either thermal or catalytic. For catalytic reactions occurring at low temperatures, the kinetic residence time is generally measured from the point of feed introduction to the point of catalytic separation, since thermal reactions are negligible. At higher temperatures where thermal reactions are not insignificant, kinetic residence time is generally measured from the point of feed introduction until the effluent is quenched following catalyst separation.

The effluent produced from this process flows through a separator where the combined product and diluent are rapidly separated from the catalyst solids and then optionally quenched by direct introduction of a quench medium to freeze the reaction. The catalyst solids from the separator are stripped of residual hydrocarbon, regenerated and reheated and returned to the top of the tubular reactor. The continuous regeneration of the catalyst provides higher intrinsic levels of activity for the system compared to fixed bed systems where there is no continuous regeneration. This further decreases system limitations caused by catalyst fouling.

The reactor velocity is determined from the volume flow of the reacting mixture (mass flow, molecular weight, P, T) and the diameter of the reactor. The velocity is limited by certain system erosion criteria and other mechanical considerations. It is known in mixing and separation processes that the length to diameter ratio (L/D) is critical. The total residence time in the system is a function of the velocity as defined above and the length of the reaction zone. For any desired residence time, the velocity-length relationship is set. The L/D ratio then sets the diameter with the specified length. The capacity of the present reactor is set by velocity criteria and the total cross-sectional area. Residence times on the order of 200 milliseconds can be achieved at capacities equivalent to other commercial dehydrogenation processes. For example, a single reactor module can process the equivalent of 130 MM lb/yr propylene from propane. Residence times greater than 200 milliseconds are possible by simply lengthening the reactor section (with the mixing and separation zones intact) or reducing the throughput. Residence times less than 200 milliseconds are possible by reducing the capacity of a given module (reducing length and thus diameter at constant velocity).

The present process is particularly well adapted for use in a low residence time fluidized solids cracking apparatus, such as those described in U.S. Pat. Nos. 4,814,067 herein by reference.

DESCRIPTION OF THE PREFERRED EMBODIMENTS

As has been previously indicated, the process of the present invention is directed to a means for producing olefins from paraffins of five or fewer carbon atoms in the presence of catalytically active dehydrogenation heat carrying solids. The description will be made in terms of propane, however, the invention covers other light hydrocarbons, such as ethane, butane, isobutane, pentane and isopentane.

Figure 1:
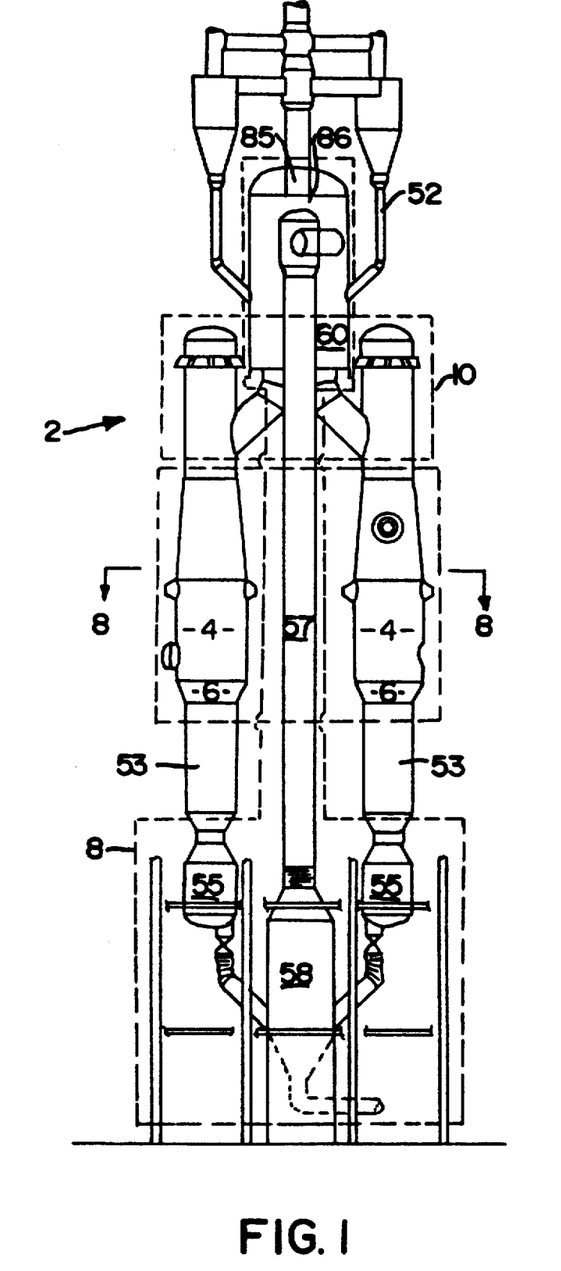
FIG. 1 is an elevational view of the overall system of the present invention.
Figures 2, 3:
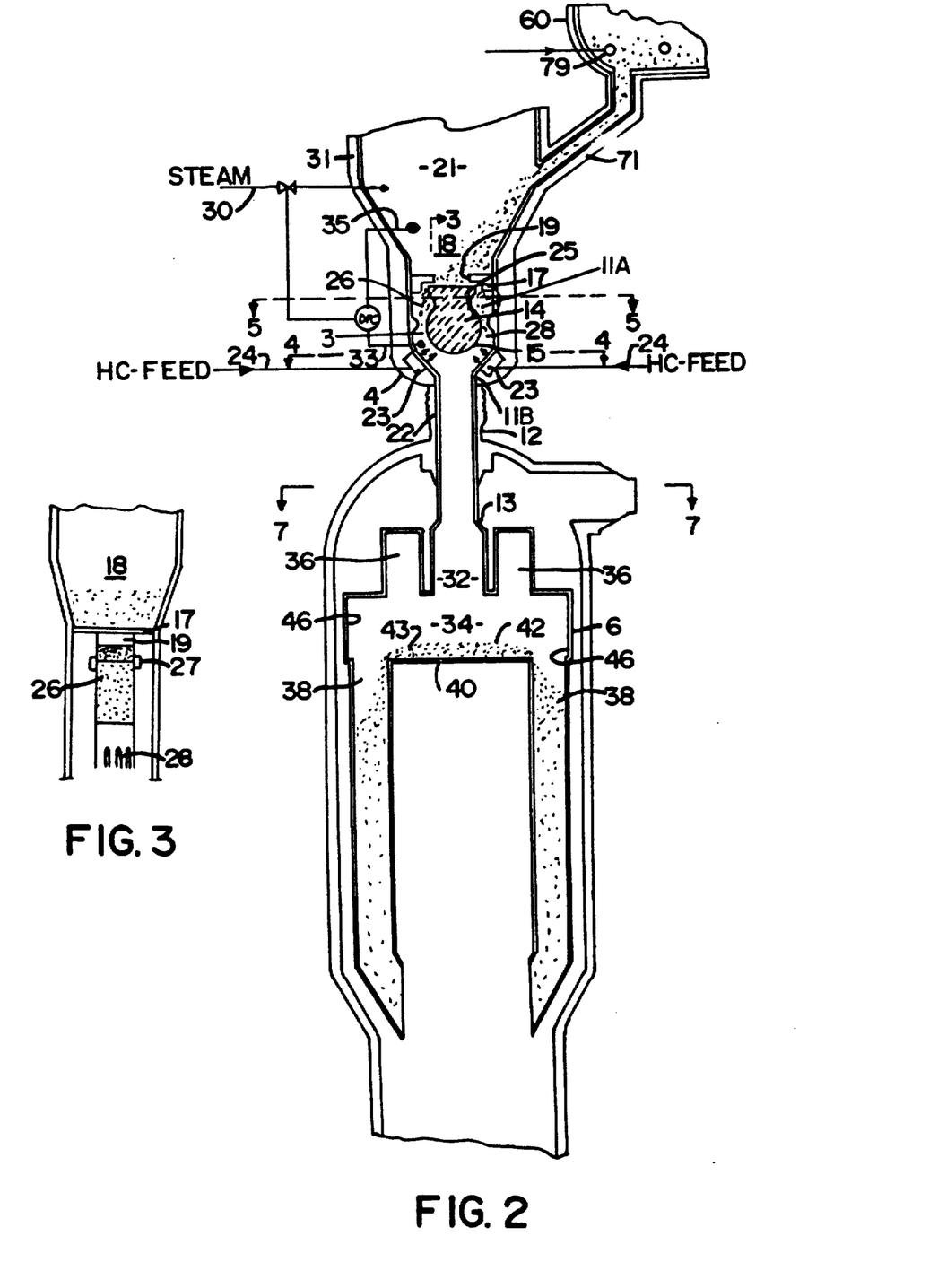
FIG. 2 is an enlarged sectional elevational view of the reactor and cracked gas-solids separator of the present invention.
FIG. 3 is a sectional elevational view through line 3—3 of FIG. 2.

As best seen in FIGS. 1 and 2, the system 2 is comprised essentially of reactor system 4, a catalyst solids regeneration assembly 8, a catalyst solids delivery system 10 and an acceleration zone 11A.

The reactor system 4, best seen in FIG. 2, includes a convergent mixing section 11B, an elongated reaction section 12, a divergent section 13 downstream of the elongated reaction section 12, a separator 6 and quench system (not shown). The acceleration section 11A and the mixing section 11B are formed with a plug member 14 shown in cross-section as having an arcuate lower surface 15. A horizontally disposed plate 17 is arranged over the plug member 14 in spaced relationship with the plug member 14 to form catalyst solids inlet passages 19 to the interior of the acceleration zone 11A. The catalyst solids inlet passages 19 are configured in cross-section with a right angle turn and terminate in rectangular openings 25 through which the catalyst solids enter the acceleration zone 11A, in the form of a curtain of catalyst solids 26 as best seen in FIG. 3. Thus, the catalyst solids inlet passages are arranged normal to the reactor centerline and thereafter at a right angle to terminate in openings parallel to the reactor centerline. The horizontal openings 25 are directly above each hydrocarbon feed inlet. Venturi configured passages 27 extend from the catalyst solids inlet passages 19 to the hydrocarbon feed inlets 28.

In preferred embodiments, a dilution or pre-acceleration gas, such as steam or other inert gas or portion of the feed, may be introduced into the curtain of catalyst solids 26 passing through the horizontal opening 25 from nozzles (not shown). The pre-acceleration or dilution gas accelerates the flow of catalyst solids through the horizontal openings 25 before contact with the main feed. The use of such an embodiment aids in mixing and heat transfer.

The hydrocarbon feed inlets 28 are located on the reactor wall 22 and are arranged either normal to the catalyst solids curtain 26 or at an angle upwardly of 30° into the catalyst solids curtain 26. The hydrocarbon feed is delivered to a manifold 23 through a line 24. The feed inlet nozzles 28 are fed with hydrocarbon from the manifold 23. As best seen in FIG. 2, the feed inlet nozzles 28 are diametrically opposed from each other in the same horizontal plane. The mixing zone 11B of the reactor is generally rectangular with the configuration making a transition to a tubular reactor at the elongated reaction section 12.

The feedstock entering the mixing zone 11B through nozzles 28 immediately impinges the accelerated catalytic solids curtain 26 and the desired mixing of feed and hot catalytic solids occurs. With the opposing set of nozzles 28, the opposing feed jets and entrained solids from the catalyst solids curtain 26 will be directed by the arcuate contour 15 of the plug member 14 and impact with each other at approximately the vertical centerline of the mixing zone 11B. When a gas-liquid mixed phase hydrocarbon is fed through the nozzles 28, the nozzles 28 are arranged at an angle normal or 90° to the catalyst solids curtain 26. When the hydrocarbon feed is a gas, the nozzles 28 are arranged at an upwardly directed angle of 30° into the catalyst solids curtain 26. The quantity of catalyst solids entering the acceleration zone 11A of the reaction system through the horizontal inlets 19 is controlled in large part by the pressure differential between the mixing zone 11B of the reaction system and the chamber 21 above the bed of catalyst solids 18 in a catalyst solids control hopper 31 directly above the horizontal inlets 19. Pressure probes 33 and 35 are located respectively in the mixing zone 11B of the reaction system and the control hopper chamber 21 to measure the pressure differential. Gas (steam) under pressure is delivered through a line 30 to the control hopper chamber 21 to regulate the pressure differential between the mixing zone 11B of the reaction system and the control hopper chamber 21 to promote or interrupt flow of the catalyst solids from the catalyst solids control hopper 31 to the mixing zone 11B of the reaction system. A detailed description of the process of regulating the solids flow is found in U.S. Pat. Nos. 4,459,071 and 4,453,865 which are incorporated herein by reference.

The hydrocarbon feed enters the mixing zone 11B of the reaction system at a temperature of approximately 60° F. and is elevated to a cracking temperature of approximately from 600° F. to 1200° F. The reaction proceeds through the mixing zone 11B and elongated cracking zone 12. Thereafter, the combined reacted effluent and entrained catalyst solids discharge into the separator 6. The residence time from entry of the hydrocarbon feedstock into the reaction system to the point of quench after separator 6 is from about 0.1 to about 2.0 seconds.

In a preferred embodiment and as best seen in FIG. 2, the separator 6 is comprised of a mixed phase inlet 32, a horizontal chamber section 34, a plurality of reacted gas outlets 36 and catalyst solids outlets 38. The separator 6 is an improvement on the solids-gas separator described in U.S. Pat. No. 4,433,984, the subject matter of which is incorporated herein by reference. The basic principles relating to relative diameters ($D_i$, $D_{og}$, $D_{os}$), chamber height (H) and length (L) recited in U.S. Pat. No. 4,433,984 again pertain. However, the separator 6 is arranged in combination with the elongated reaction zone 12 and divergent section 13 of the reaction system. The divergent section 13 of the reaction system terminates in the separator mixed phase inlet 32 which is centrally disposed at the top of the horizontal section 34. As a result of the configuration of the composite reaction system including the separator 6, a catalyst solids bed 42 develops on the floor 40 of the horizontal section 34 with the cross-sectional profile 43 of the bed 42 forming a curvilinear arc over which the mixed phase gas and catalyst solids travel. The expansion of catalyst solids and reacted gas in the divergent section 13 enhances heat transfer and limits the velocity of the catalyst solids-gas mixture entering the separator 6.

The catalyst solids are discharged to the lateral ends 46 of the horizontal section 34 and flow downwardly through the catalyst solids outlets 38. The reacted gases follow a 180° path and after separation from the catalyst solids and discharge through reacted gas outlets 36 that are located on the top of the horizontal section 34 intermediate the lateral ends 46. The plurality of catalyst solids outlets 38 and reacted gas outlets 36 provide simultaneously for both minimum time in the separation zone and maximum catalyst solids-gas separation.

The separation system may also include conventional cyclone separators (not shown) directly downstream of each reacted gas outlet 36. The cyclone separators serve to collect the remaining entrained catalyst solids from the reacted gas discharged from the separator 6. A dipleg line may be employed to return the catalyst solids to the downstream regeneration assembly 8 and the separated reacted gas is sent for downstream processing.

In practice, the separator 6 separates 95 to 99% of the catalyst solids from gas-solids mixtures having dust loadings of 0.2 to 0.3 pounds of solid per cubic foot of gas where the average particle size of the solids is 90 microns.

The reacted gas outlets 36 may be provided with a direct quench line or the quench may be added in the cyclone separators. Quench oil, usually the 100°-400° F. cut from a downstream distillation tower is introduced to terminate the reactions of the reacted gas. Preferably 0.1 to 0.3 pounds of quench oil are introduced into the reacted gas outlets 36 or cyclone separators for every pound of reacted gas.

In practice, it has been found that the reaction time; i.e. effective kinetic residence time, is the time that elapses from the introduction of feed into the reaction system until the termination of gas reactions at quenching. The effective kinetic residence time includes the time during which the hydrocarbon and catalyst solids are in intimate contact and the time from separation until quench. The effective kinetic residence time in processes of the present invention is 0.1 to 2.0 seconds.

Figure 4:
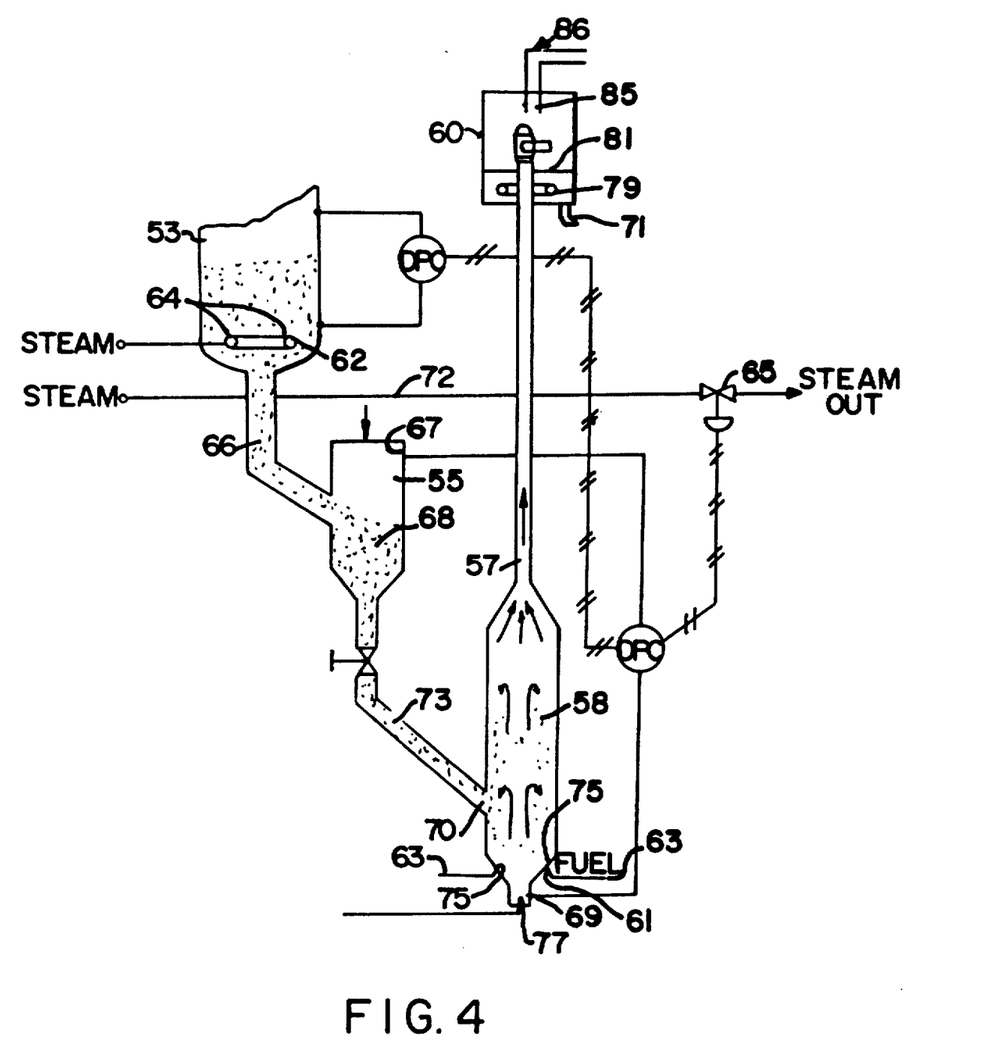
FIG. 4 is a schematic elevational view of the solids regeneration assembly.

As best seen in FIG. 4, the regeneration assembly 8 is preferably comprised of a stripper 53, control hopper 55, entrained bed heater 58, a lift line 57, and a regenerated catalyst solids vessel 60 although a variety of regeneration assemblies are contemplated.

The stripper 53 is a tubular vessel into which the catalyst solids from the separator 6 are delivered through catalyst solids outlet legs extending from the separator solids outlets 38 and from the cyclone diplegs. A ring 62, best seen in FIG. 4, having nozzle openings 64, is provided at the bottom of the stripper 53. A stripping gas, typically steam, is delivered to the ring 62 for discharge through the nozzles 64. The stripping steam passes upwardly through the bed of catalyst solids to remove impurities from the surface of the catalyst solids. Preferably 1.0 to 3.0 pounds of steam at 200° C. to 500° C. and 20 to 200 psig pressure are delivered to the stripper for each 0.5 ton of catalyst solids. The stripping steam and entrained impurities pass upwardly through the catalyst solids in the stripper 53 and discharge through a vent line (not shown).

The stripped catalyst solids are accumulated in the control hopper 55 for eventual delivery to the entrained bed heater 58. The control hopper 55 is a collection vessel in which catalyst solids enter through the standpipe 66 in unaerated flow and from which an outlet line 73 extends to deliver catalyst solids to the entrained bed heater 58. The assembly of the control hopper 55 and standpipe 66 provides for a slumped bed solids transport system as described in U.S. Pat. Nos. 4,459,071 and 4,453,865, which are incorporated herein by reference. The pressure differential maintained between the slumped bed surface 68 in the control hopper 55 and the exit 70 of the outlet line 73 determines the catalyst solids flow rate between the control hopper 55 and the entrained bed heater 58. A line 72 is provided to selectively introduce steam under pressure into the control hopper 55 to regulate the pressure differential. Probes 67 and 69 are placed respectively in the control hopper 55 and entrained bed heater 58 to monitor the pressure differential and regulate the valve 65 in the steam line 72.

The entrained bed heater 58 is essentially tubular in configuration. An array of distinct fuel nozzles 61 fed by fuel lines 63 are arranged essentially symmetrically on the lower inclined surface 75 of the entrained bed heater 58. Air under pressure enters the entrained bed heater 58 through a nozzle 77 arranged to direct the air axially upwardly through the entrained bed heater 58. The air jet provides both the motive force to lift the catalyst solids particles upwardly through the entrained bed heater 58 to the regenerated catalyst solids vessel 60 and the air necessary for combustion. The fuel is ignited by contact with the hot solids in the presence of air.

The combustion gas/solids mixture moving upwardly through lift line 57 enters the regenerated solids vessel 60 tangentially, preferably, perpendicular to the lift line to separate the combustion gases from the solids. As shown in FIG. 1, the vessel 60 has a distube 85 in the gas outlet nozzle 86 to provide cyclonic movement which improves the separation efficiency of the system. Catalyst solids flow to Hopper 31 through 71.

In operation, the catalyst solids slide down the inside edge of the entrained bed heater 58 and are picked up by the central air jet which operates at a velocity of 80 to 150 feet per second. The superficial velocity in the main body of the entrained bed heater 58 is 8 to 15 feet per second. The reduction in velocity and the use of a single central jet creates a circulation in dilute phase within the expanded portion of the bed. The entrained catalyst solids fall to the side and are re-entrained in the jet. The velocities are such that there is a net transport of catalyst solids up the lift line 57 with the wide spot in the line creating a zone of recirculation and hence higher catalyst solid density and residence time. Practice shows that the catalyst solids on the average recirculate about 10 to 15 times compared to the net throughput. The characteristics and advantages of the entrained bed heater 58 include a recirculation system that creates a higher catalyst solids density that reduces peak temperature which could damage catalyst solids. In addition, the combustion in the entrained bed heater 58 occurs in the gas phase. The catalyst solids are suspended in the gas and thus the combustion is rapid and the gas and fuel are intimately mixed in the combustion zone.

The combustion reaction in the entrained bed heater includes the coke coating the catalyst solids. Thus, the feed to air ratio is maintained for a nominal 10% excess of air over fuel and insures that all the coke on the catalyst solids is burned and contributes to the catalyst solids heating process.

The regenerated catalyst solids vessel 60 is a cylindrical vessel provided with a standpipe 71, seen in FIG. 2, extending to the reactor hopper 31. Again the structure of the regenerated catalyst solids vessel 60 provides for stripping the catalyst solids by steam or other gases in a bed 81, seen in FIG. 4. Stripping gases enter via distributor 79, located in the base of the bed. From the stripping section the catalyst solids flow via an unaerated standpipe 71 to control hopper 31.

The catalyst solids flow from the rectangular orifices or catalyst solids inlet passages 19 in what can be described as extrusion flow. The catalyst solids are in dense phase until picked up by the pre-acceleration gas. A pressure drop of 0.5 to 5.0 psi is used to control the rate of catalyst solids flow to the reactor mixing section 11B.

In a preferred embodiment the process of the invention proceeds by delivering pre-acceleration gas feed such as steam at a temperature of from about 300° to about 1000° F. through the pre-acceleration inlets, and hydrocarbon feed, such as propane, at a temperature of from about 300° to about 1000° F., through the feed nozzles 28 to the reactor 4. The hot catalyst solids are delivered to the reactor 4 through the rectangular orifices at a temperature of from about 1000° to 1800° F. The hydrocarbon feed mixes with the hot catalyst solids and is reacted at a temperature of from about 600° to about 1400° F. The pressure in the reactor is from about 10 to about 100 psi and the residence time or contact time from hydrocarbon feed entry to quenched reacted gas effluent is from about 0.1 to about 2.0 seconds. The hot catalyst solids are cooled from their inlet temperature to the reaction temperature and spend from about 0.1 to about 2.0 seconds from passage through the rectangular orifice to discharge from the separator solids outlet.

The quench reduces thermal reactions. Catalyst solids separation reduces catalytic reactions. If the temperature is below 1000° F., thermal reactions are negligible and a quench is generally not necessary. The effluent gases can be quenched by direct quench oil to below from about 1000° F. to about 1100° F. Thereafter, additional quench cooling is optionally performed to reduce the effluent temperature to temperatures required for fractionation.

The catalyst solids are stripped of surface impurities in the stripper by steam at temperatures of from about 1100° to about 1500° F. The stripped catalyst solids are then delivered to the entrained bed heater at a temperature of from about 1100° to about 1500° F. Fuel having a BTU content of 17,000–22,000 BTU/LB and 12 to 17 pounds of air per pound of fuel and coke are continuously fed to the entrained bed heater and combusted with the coke (carbon) on the catalyst solids at temperatures of 1200° to 1700° F. and a pressure of 6 to 60 psi. Hot catalyst solids are delivered to the regenerated solids vessel at a temperature of 1000° to 1800° F. where the combustion gases are separated in cyclones and exhausted as flue gas. The flue gas has no BTU content and is used to preheat feedstock or generate steam.

The hot catalyst solids are returned to the reactor 4 through the reactor hopper and rectangular orifices at a temperature of from about 1000° to about 1800° F.

The process of the present invention increases the amount of effective catalyst surface area available for reaction, by allowing for the utilization of smaller catalyst particles. Catalytic reactions are a direct function of catalyst surface area, and small catalyst particles have more external surface area per pound of catalyst than large catalyst particles. The system of the present invention is capable of using fluidizable catalyst solids with an average particle size ranging from about 20 microns to about 500 microns, and a surface area in the range of from about 20 m²/g to approximately 450 m²/g; as well as the 10,000 micron diameter catalyst beads conventionally employed in fixed or moving bed processes to minimize pressure drop.

The use of smaller catalyst particles results in an enhanced conversion in shorter residence times than is achievable in a fixed bed reactor. The smaller catalyst particle size associated with the present invention improves the mass transfer to the catalyst compared to larger particles by presenting more external surface per unit mass of catalyst and by reducing pore diffusion resistance (shorter pores).

The present invention also overcomes the inherent limitations of current reactor technology arising from relatively large pressure drops. Dehydrogenation reaction kinetics are favored by low pressure. The present invention is capable of achieving essentially plug flow reaction conditions with essentially no pressure drop in the reactor zone. Therefore, the reaction can be run at short residence times, with high heat input, with low pressure drops, and using small solids, all of which is unobtainable with fixed beds.

The present invention also allows for an enhanced temperature profile control within the reaction zone. This is achieved by independently controlling the incoming temperature and/or flow of the catalyst particles.

Another advantage of the present invention is its ability to continuously regenerate catalyst due to the circulating nature of the invention.

The catalyst employed in the system for the dehydrogenation of propane may be iron, nickel, palladium, platinum, vanadium, chromium, manganese, $K_2O$, tin oxides, and/or lead oxides, and the like. Preferably the catalyst has high or moderate dehydrogenation activity.

A suitable support for the dehydrogenation of propane may be one of the generally available carriers such as $Al_2O_3$, Kaolin, amorphous clay, or combinations of the above with or without aluminosilicate zeolites.

A preferred catalyst, useful in the practice of the present invention, comprises a palladium-alumina ($Pd$—$Al_2O_3$) catalyst. The preferred catalyst can be obtained by loading the alumina support with 15 weight percent of palladium, pretreating the catalyst by a dry hydrogen reduction method, adding a sulfur dioxide promoter. Further the preferred catalyst has a surface are of 450 m²/g. Such a palladium catalyst has an activity of about 142.

Further catalysts of the present invention can be prepared by varying the surface area, the metal loading, method of reducing the support and by choice and amount of promote. In this manner, catalysts having moderate to high activity, as defined herein, can readily be prepared by those skilled in the art.

EXAMPLES

A kinetic computer model was developed to further demonstrate the present invention. The model incorporates two catalytic dehydrogenation reactions (ethane and propane) and fifteen thermal reactions.

In order to validate the model, output was compared to actual thermal cracking runs. These runs were made on a bench scale adiabatic solids cracking unit.

Table 1 compares the yield of an actual thermal cracking yield with the yield determined by the model. The results are quite close in the range of interest.

The model output was also compared against published information on a commercial moving bed reactor for propane dehydrogenation. This reactor consists of three separate charge heaters (one feed preheater and two reaction interstage heaters) and three catalyst zones. The temperatures and inlet/outlet pressures were known, and residence times in the various sections were assumed or calculated based on pressure drop. The moving bed reactor profiles are presented in Table 2 and the yield comparison is presented in Table 3.

The kinetic expressions for the catalytic reactions were taken from literature. The general expression for the catalytic dehydrogenation reaction is Rate=A * EXP (−E/RT) * (catalyst area) * (equilibrium factor) * (partial pressure)$^{0.66}$ * (activity factor)

The first part of the equation is the common Arrhenius expression for the rate constant. The pre-exponential factor was adjusted to give the closest approximation to actual commercial moving bed yields.

The second term, catalyst area, measures the quantity of catalyst available for the reaction. The literature rate expression used the simplifying assumption that the reaction is proportional to the area. There is no distinction made between gas film resistance, pore diffusion resistance, etc. This assumption is conservative in that pore diffusion would impact large fixed bed particles more than small catalyst as used in the process of the present invention.

For a fixed bed, a voidage of 0.5 is assumed and the catalyst volume is thus equal to the reactant volume. The catalyst weight is determined from the catalyst volume and the particle density. The surface area in square meters is then determined from the specific surface.

For the flowing reactor, the gas density and the weight ratio of solid to hydrocarbon defines the catalyst weight for the section. For the flowing reactor, the catalyst surface is approximately an order of magnitude less than the fixed bed.

The third term, equilibrium factor, is a measure of the driving force for the reaction. The partial pressure ratio at any point is defined as:

$$K_p = pH_2 * pC_3H_6 / pC_3H_8$$

Kp has a limiting value at thermodynamic equilibrium (Kp equil). The approach to equilibrium is thus (Kp actual/Kp equil) and the driving force for the reaction is (1−Kp actual/Kp equil). At equilibrium, the driving force for the reaction is zero.

The reaction order (0.66) was based on literature findings. The activity factor is simply a multiplier to allow investigation of more active catalysts than commercial catalysts as specified by the A and E selected. In this case, the activity factor is equal to 1.0.

The model is not designed for a specific catalyst but allows input of catalyst properties to permit for flexibility in attaining desired product characteristics. No specific catalyst formulation is implied in these calculations. The model calculations use a combination of specific surface and activity factor (multiplier to the rate) to set different catalyst properties. The calculations used, for example, set the specific surface of the fixed bed catalyst ($250M^2/gm$) for all cases. An actual fluidizable dehydrogenation catalyst may have a lower specific surface for mechanical reasons which would reduce the overall catalytic rate and require a catalyst having a higher activity factor. The flow of solids into the transport system of the process is a variable which affects the total catalyst surface available for the reaction. The process of the subject invention is capable of using many types of catalysts with varying activities as long as they possess certain mechanical properties to allow for circulation. The process is much more flexible than fixed bed, tubular, or moving bed reactors in this regard since with the ability to add heat to the reaction with the solids, the ratio of thermal to catalytic reactions can be changed not only by raising or lowering the temperature but by changing the flowing catalyst density.

Figure 5:
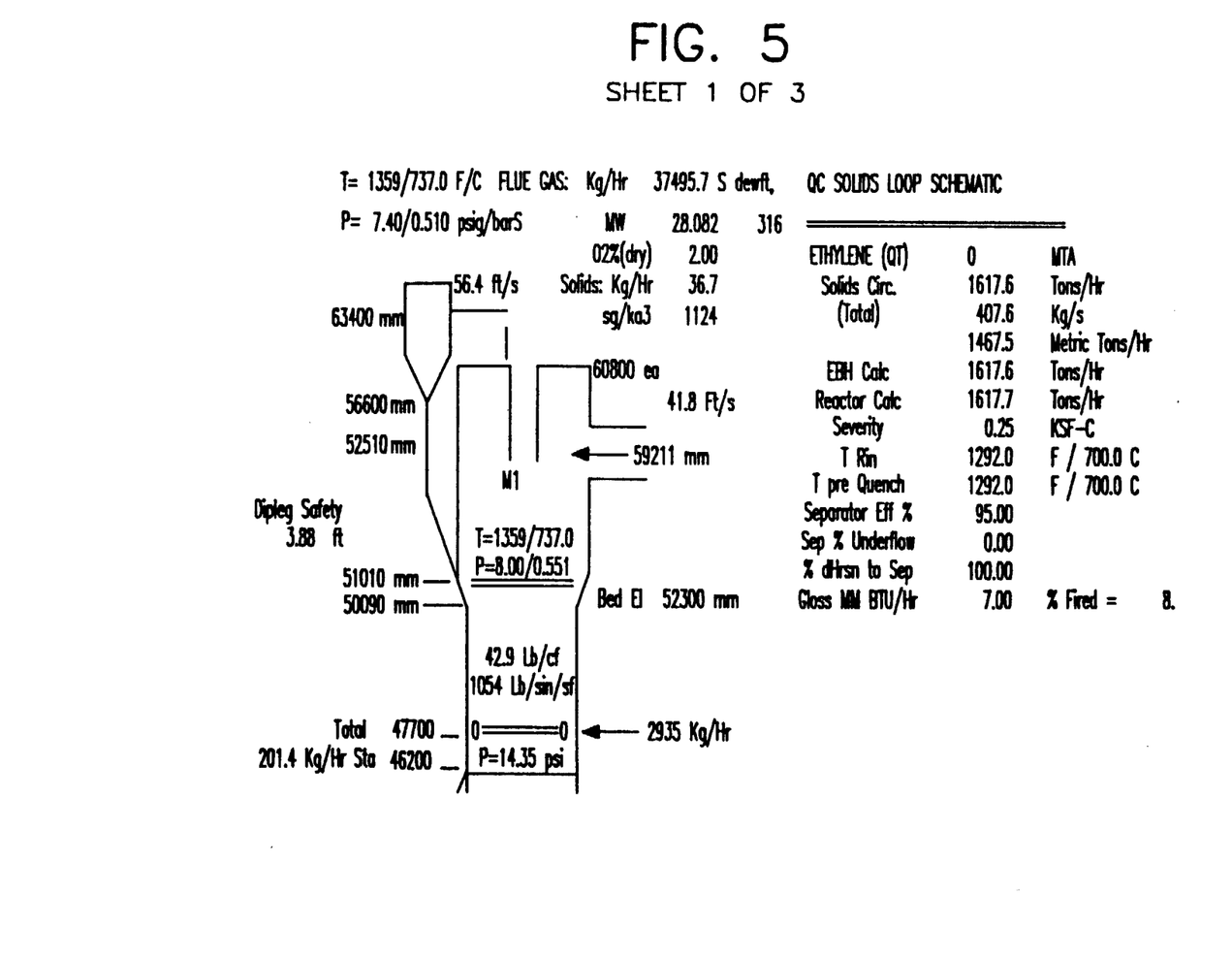
FIG. 5 shows a heat and mass balance performed on a preferred embodiment of the present invention. Sheet 1 of FIG. 5 is the highest elevational portion of the preferred system for running the process of the present invention, sheet 2 of FIG. 5 is the lowest elevational portion of the preferred system for running the process of the present invention.

In order to illustrate the advantages of the process for dehydrogenation of the present invention, a number of cases have been examined for the quick contact (QC) type short residence time system of the present invention; and a moving bed system of the prior art, and a flowing solids dilute phase riser reactor system. The riser reactor assumes a catalyst to feed ratio of 10 and a residence time of 2.0 seconds consistent with the operating conditions one might experience if the reaction were carried out in a conventional riser FCC system. The results are summarized in Table 4. The feedstock flow, the dilution level, and the outlet pressure were held constant for all of these cases. The results of an overall QC heat balance for a single case (Case 5) assuming a 50° C. temperature drop over the reactor length and a solids/hydrocarbon ratio of 70 are set forth in FIG. 5.

It should be noted that all cases have been run with a standard feed composition. In actual fact, the moving bed cases must have more dilution than shown as illustrated by the "actual" moving bed case shown in Table 4. Also, the QC examples presented are operated at high conversion levels (i.e. approximately 80-85%). The moving bed cases are either the practical conversion limit (Case 8) or hypothetical cases constructed to illustrate specific advantages for QC. The hypothetical cases are inoperable due to catalyst fouling as noted by the high yield of $C_{5=}$ for cases 9 and 11. Since regeneration is limited due to the low solids circulation, higher yields of fouling components cannot be tolerated.

The riser case uses a low solids flow compared to QC since it operates in upflow compared to downflow. In upflow, catalysts tend to cluster and fall back, creating higher density but with cooler catalysts. Limits of pneumatic conveying in upflow set this circulation rate. With lower solids flow, the solids must enter the reactor considerably hotter in order to transfer the same heat as a comparable QC reactor operating with high solids flow. This leads to higher thermal reactions.

The residence time employed in catalytic reactions in a flow reactor depends upon the catalyst activity level. In other words, at any conversion level, the catalytic reaction must dominate. With a low catalyst activity, a longer time is required to achieve desired conversions since temperatures must be low to reduce thermal reactions as well. With high activity catalysts, a shorter time is preferred to benefit from equilibrium relationships while avoiding excessive thermal reactions.

A QC type processing system can surprisingly realize specific and unique advantages compared to either fixed bed, moving bed, or tubular reaction systems. These flow from the limits of these processes to allow for heat input or regenerate catalyst or both in a continuous fashion. It is also considerably superior to a riser type reactor since higher flowing catalyst densities are possible. Further the QC type process can achieve higher ultimate yields (selectivity) to the feed carbon number olefin.

Further, in order to operate at short time, the process must be able to add heat continually to the process. This is not possible with fixed or moving bed systems. Heat can be added to tubular reactors (at high mechanical complexity) but they cannot regenerate the catalyst and are hence inoperable as well, unless operated in cycles requiring added units for regeneration plus complicated valving systems to shift between on-stream and off-stream reactors.

Conventional technology is limited to either pyrolysis or dehydrogenation (shaded areas). Short or moderate pyrolysis reactors with high heat input cannot be filled with catalyst due to excessive pressure drops. They must operate in a thermal mode only. The yield structure is predominately cracking (smaller olefins than the feed) compared to dehydrogenation. Dehydrogenation reactors cannot operate in a cracking mode because high temperatures and cracking lead to fouling and require high heat input. Thus the yield structure is predominately dehydrogenation (olefins of the same carbon number as the feed).

QC is unique in its ability to transcend the limits and operate in either regime or a combination of the two regimes. By changing catalyst activity or catalyst flow rate (catalyst density) and the operating temperature (vary heat input), the yield pattern for propane can be shifted from propylene to ethylene. This is contrary to the teachings of conventional technology.

The above-mentioned patents and publications are incorporated herein by reference.

The foregoing detailed description will suggest many obvious variations to those skilled in the art. For example, the catalyst used in this process can be added at a point somewhat below the top of the tubular downflow reactor. The catalyst employed may be conventional, moderate activity or high activity. Any down flow short residence time reactor or separation system known to those skilled in the art is contemplated. A paraffin feed may be utilized having minor amounts of paraffins having different numbers of carbon atoms. All such obvious modifications are within the full intended scope of the appended claims.

TABLE 1

| Kinetic Validation Thermal Reactions Only | | |
|---|---|---|
| | QC PYROLYSIS | MODEL |
| Yield, wt % | | |
| $H_2$ | 0.22 | 0.22 |
| $CH_4$ | 2.38 | 2.98 |
| $C_2H_4$ | 4.10 | 5.08 |
| $C_2H_6$ | 0.32 | 0.27 |
| $C_3H_6$ | 5.50 | 4.63 |
| $C_3H_8$ | 86.85 | 86.17 |
| OPERATING CONDITIONS | | |
| RTU OUTLET TEMP, °C. | 719 | |

TABLE 1-continued

Kinetic Validation Thermal Reactions Only

| | QC PYROLYSIS | MODEL |
|---|---|---|
| MODEL ISOTHERMAL TEMP, °C. | | 740 |
| TIME, SEC | 0.36 | 0.36 |
| P, ATM | 1.55 | 1.55 |
| S/HC | 0.20 | 0.20 |

*bench scale adiabatic reactor using inert solids as a heat carrier.

TABLE 2

Reactor Profile for Moving Bed Pressure

TABLE 3

Yield Comparison Catalytic Moving Bed vs Model

| Field, wt % | MOVING BED | MODEL |
|---|---|---|
| $H_2$ | 4.8 | 4.8 |
| $CH_4$ | 5.5 | 5.5 |
| $C_2$'S | 1.1 | 1.1 |
| $C_3H_6$ | 1.0 | 1.0 |

TABLE 3-continued

Yield Comparison Catalytic Moving Bed vs Model

| | MOVING BED | MODEL |
|---|---|---|
| $C_3H_8$ | 87.6 | 87.6 |
| Effluent, wt % | | |
| $H_2$ | 6.0 | 6.05 |
| $CH_4$ | 6.9 | 6.99 |
| $C_2$'S | 3.5 | 3.59 |
| $C_3H_6$ | 29.1 | 27.15 |
| $C_3H_8$ | 54.5 | 55.39 |
| $C_4$'S | not available | 0.10 |
| $C_5+$ | not available | 0.73 |
| Total | 100.00 | 100.00 |

TABLE 4

| | QC* Pyrolysis Case 1 | QC CATALYTIC | | | | | Riser Reactor | MOVING BED REACTOR | | | | QC | | | | | |
|---|---|---|---|---|---|---|---|---|---|---|---|---|---|---|---|---|---|
| | | Case 2 | Case 3 | Case 4 | Case 5 | Case 6 | | Actual Case 7 | Case 8 | Case 9$^a$ | Case 11$^a$ | Case 12 | Case 13 | Case 14 | Case 15 | Case 16 | Case 17 |
| Feed, mol | | | | | | | | | | | | | | | | | |
| $C_3H_8$ | 0.58 | 0.58 | 0.58 | 0.58 | 0.58 | 0.58 | 0.58 | 0.41 | 0.58 | 0.58 | 0.58 | 0.58 | 0.58 | 0.58 | 0.58 | 0.58 | 0.58 |
| $H_2$ | | | | | | | | 0.50 | | | | | | | | | |
| $CH_4$ | | | | | | | | 0.07 | | | | | | | | | |
| STM | 0.42 | 0.42 | 0.42 | 0.42 | 0.42 | 0.42 | 0.42 | — | 0.42 | 0.42 | 0.42 | 0.42 | 0.42 | 0.42 | 0.42 | 0.42 | 0.42 |
| Yield Wt % | | | | | | | | | | | | | | | | | |
| $H_2$ | 1.27 | 1.79 | 3.08 | 3.13 | 3.90 | 3.63 | 2.14 | 6.05 | 1.80 | 3.27 | 2.41 | 3.36 | 3.60 | 3.40 | 3.79 | 3.77 | 1.29 |
| $CH_4$ | 21.79 | 16.93 | 10.21 | 6.18 | 1.83 | 1.82 | 16.75 | 7.00 | 1.82 | 10.32 | 2.28 | 5.96 | 6.05 | 1.69 | 3.50 | 1.35 | 21.74 |
| $C_2H_2$ | 0.51 | 0.43 | 0.37 | 0.29 | 0.17 | 0.17 | 0.58 | nil | 0.14 | 0.51 | 0.19 | 0.32 | 0.38 | 0.17 | 0.27 | 0.14 | 0.52 |
| $C_2H_4$ | 36.11 | 27.65 | 13.89 | 6.50 | 0.67 | 0.50 | 22.45 | 2.11 | 1.41 | 6.71 | 2.33 | 4.35 | 2.19 | 0.29 | 0.74 | 0.93 | 35.99 |
| $C_2H_6$ | 2.36 | 2.14 | 2.44 | 2.56 | 1.12 | 1.35 | 5.29 | 1.44 | 1.53 | 6.73 | 10.38 | 3.49 | 4.50 | 1.28 | 2.17 | 0.88 | 2.40 |
| $C_3H_6$ | 15.87 | 24.48 | 44.81 | 51.58 | 72.82 | 68.31 | 27.25 | 27.13 | 36.86 | 41.34 | 52.53 | 53.56 | 53.07 | 63.51 | 60.76 | 74.28 | 16.08 |
| $C_3H_8$ | 14.57 | 18.43 | 13.52 | 20.69 | 13.70 | 18.84 | 12.79 | 55.37 | 54.41 | 12.49 | 23.06 | 17.72 | 15.44 | 24.41 | 17.36 | 15.27 | 14.29 |
| $C_4$ | 2.77 | 2.09 | 1.61 | 0.96 | 0.49 | 0.45 | 2.26 | 0.10 | 0.30 | 1.50 | 0.41 | 0.99 | 1.06 | 0.41 | 0.75 | 0.39 | 2.79 |
| $C_5$ | 4.80 | 6.04 | 10.06 | 8.11 | 5.29 | 4.93 | 10.49 | 0.73 | 1.71 | 17.12 | 6.40 | 10.26 | 13.71 | 4.84 | 10.65 | 2.98 | 4.91 |
| Operating Conditions | | | | | | | | | | | | | | | | | |
| Catalyst Activity | None | 20 | 100 | 100 | 1000 | 1000 | 100 | 1 | 1 | 1 | 50 | 100 | 100 | 1000 | 1000 | 1000 | 1 |
| Time, Sec. | 0.25 | 0.25 | 0.25 | 0.50 | 0.25 | 0.50 | 2.0 | 5.7 | 5.7 | 5.7 | 5.7 | 1.0 | 2.0 | 1.0 | 1.0 | 0.10 | 0.25 |
| Tout, °C. | 815 | 800 | 775 | 725 | 700 | 675 | 650** | 641 | 641 | 689 | 641 | 700 | 675 | 650 | 675 | 725 | 815 |
| P, ATM | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 | 1.6 |
| Conversion | 85.5 | 81.6 | 86.5 | 79.3 | 86.3 | 81.2 | 87.2 | 36.7 | 45.6 | 87.5 | 76.9 | 82.3 | 84.6 | 75.6 | 82.6 | 84.7 | 85.7 |
| Ultimate Yield | 18.6 | 30.0 | 51.8 | 65.0 | 84.4 | 84.1 | 31.25 | 73.9 | 80.8 | 47.2 | 68.3 | 65.1 | 62.7 | 84.0 | 73.6 | 87.7 | 18.8 |
| Flow Ratio Compression | 1.17 | 1.23 | 1.16 | 1.26 | 1.16 | 1.23 | — | 2.72 | 2.19 | 1.15 | 1.30 | 1.22 | 1.18 | 1.32 | 1.21 | 1.18 | 1.17 |
| Ultimate Total Olefin Yield ($C_2 + C_3$, wt %) | 60.79 | 63.88 | 67.89 | 73.24 | 85.16 | 84.74 | 56.99 | 79.67 | 83.93 | 55.60 | 71.34 | 70.36 | 65.32 | 84.39 | 74.46 | 88.80 | 60.76 |

*Inert Solid- No Catalyst **Note inlet temp. of solids much higher than QC cases to meet heat balance.
$^a$Hypothetical cases for comparison only; not operable.

| | Temp, °C. | Atm | Time, sec |
|---|---|---|---|
| Inlet | 590 | 2.32 | 0.0 |
| Outlet Fd Htr | 660 | 2.12 | 0.4 |
| Outlet 1st Cat Zone | 570 | 2.06 | 1.4 |
| Outlet Htr | 660 | 1.93 | 2.3 |
| Outlet 2nd Cat Zone | 600 | 1.86 | 3.3 |
| Outlet Htr | 660 | 1.82 | 3.7 |
| Outlet 3rd Cat Zone | 640 | 1.68 | 4.7 |
| Outlet Quench | 550 | 1.60 | 5.7 |

We claim:

1. A process for producing olefins from a paraffin having five or fewer carbon atoms, comprising:
    (a) introducing a dehydrogenation catalyst to the top of a tubular downflow reactor to produce a fluidized catalyst stream;
    (b) introducing a feed stream comprising a paraffin having five or fewer carbon atoms into the catalyst stream at a feed introduction point;
    (c) mixing the catalyst stream and the feed stream in a mixing zone to produce a mixed stream;
    (d) passing the mixed stream downward through a reaction zone at a temperature of from about 900° F. to about 1600° F. and a pressure of from about 10 to about 100 psig to produce an effluent comprising olefins; and
    (e) passing the effluent through a separator to separate the catalyst from the effluent, thereby producing a separated catalyst stream and a clean effluent stream;

wherein the kinetic residence time of said process is from about 0.1 to about 2.0 seconds.

2. A process as defined in claim 1, wherein said process further comprises a step of:
   (f) quenching the clean effluent stream with a quench medium.

3. A process as defined in claim 1, wherein said process further comprises a step of:
   (g) regenerating and reheating the catalyst of said separated catalyst stream, and then returning said catalyst to the top of the tubular downflow reactor.

4. A process as defined in claim 1, wherein the catalyst of step (a) is at a temperature of from about 1300° F. to about 1800° F., and the weight ratio of catalyst to feed in the mixed stream of step (c) is from about 5 to about 100.

5. A process as defined in claim 1, wherein said catalyst of step (a) is accelerated prior to the feed introduction point.

6. A process as defined in claim 1, wherein said feed introduction point of step (b) is in the mixing zone of step (c).

7. The process as defined in claim 1, wherein said catalyst is selected from the group consisting of metal from the transition metal group, a metal oxide from the transition metal group, an alkali compound, a tin oxide, a lead oxide and combinations of the foregoing.

8. The process as defined in claim 7, wherein said catalyst is selected from the group consisting oxide, nickel, nickel oxide, palladium, palladium oxide, platinum, platinum oxide, vanadium, vanadium oxide, chromium, chromium oxide, manganese, manganese oxide, potassium oxide, and combinations of the foregoing.

9. A process as defined in claim 7, wherein said catalyst is supported upon an inert carrier, and said inert carrier is selected from the group consisting of aluminum oxide, kaolin, amorphous clay, and combinations of the foregoing.

10. A process as defined in claim 7, wherein said catalyst further comprises an aluminosilicate zeolite.

11. A process as defined in claim 7, wherein said catalyst comprises particles from about 20 to about 500 microns in diameter, and have a surface area of from about 20 to about 450 m$^2$/g.

12. A process as defined in claim 1, wherein there is no input of heat by indirect means.

13. A process as defined in claim 1 further comprising the steps of:
   (f) quenching the clean effluent stream with a quench medium; and
   (g) regenerating and reheating the catalyst of said separated catalyst stream, and then returning said catalyst to the top of the tubular downflow reactor;
wherein the catalyst of step (a) is accelerated prior to the feed introduction point and is at a temperature of from about 1300° F. to about 1800° F. and is selected from the group consisting of a metal from the transition metal group, a metal oxide from the transition metal group, an alkali compound, a tin oxide, a lead oxide and combinations of the foregoing, and wherein said catalyst comprises particles of from about 20 to about 500 microns in diameter, having a surface area of from about 20 to about 450 m$^2$/g, and wherein there is no input of heat by indirect means.

14. A process for producing an olefin from a corresponding paraffin having five or fewer carbon atoms, comprising:
   (a) introducing a high activity dehydrogenation catalyst to the top of a tubular downflow reactor to produce a fluidized catalyst stream;
   (b) introducing a feed stream comprising a paraffin having five or fewer carbon atoms into the catalyst stream at a feed introduction point;
   (c) mixing the catalyst stream and the feed stream in a mixing zone to produce a mixed stream;
   (d) passing the mixed stream downward through a reaction zone at a temperature of from about 900° F. to about 1300° F. and a pressure of from about 10 to about 100 psig to produce an effluent comprising olefins; and
   (e) passing the effluent through a separator to separate the catalyst from the effluent, thereby producing a separated catalyst stream and a clean effluent stream;
wherein the kinetic residence time of said process is from about 0.1 to about 0.5 seconds.

15. A process as defined in claim 14, wherein said process further comprises a step of:
   (f) quenching the clean effluent stream with a quench medium.

16. A process as defined in claim 14, wherein said process further comprises a step of:
   (g) regenerating and reheating the catalyst of said separated catalyst stream, and then returning said catalyst to the top of the tubular downflow reactor.

17. A process as defined in claim 14, wherein the catalyst of step (a) is at a temperature of from about 1300° F. to about 1800° F., and the weight ratio of catalyst to feed in the mixed stream of step (c) is from about 5 to about 100.

18. A process as defined in claim 14, wherein said catalyst of step (a) is accelerated prior to the feed introduction point.

19. A process as defined in claim 14, wherein said feed introduction point of step (b) is in the mixing zone of step (c).

20. The process as defined in claim 14, wherein said catalyst is selected from the group consisting of a metal from the transition metal group, a metal oxide from the transition metal group, an alkali compound, a tin oxide, a lead oxide and combinations of the foregoing.

21. The process as defined in claim 20, wherein said catalyst is selected from the group consisting of iron, iron oxide, nickel, nickel oxide, palladium, palladium oxide, platinum, platinum oxide, vanadium, vanadium oxide, chromium, chromium oxide, manganese, manganese oxide, potassium oxide, and combinations of the foregoing.

22. A process as defined in claim 20, wherein said catalyst is supported upon an inert carrier, and said inert carrier is selected from the group consisting of aluminum oxide, kaolin, amorphous clay, and combinations of the foregoing.

23. A process as defined in claim 20, wherein said catalyst further comprises an aluminosilicate zeolite.

24. A process as defined in claim 20, wherein said catalyst comprises particles from about 20 to about 500 microns in diameter, and have a surface area of from about 20 to about 450 m$^2$/g.

25. A process as defined in claim 14, wherein there is no input of heat by indirect means.

26. A process as defined in claim 14, further comprising steps of:
   (f) quenching the clean effluent stream with a quench medium; and
   (g) regenerating and reheating the catalyst of said separated catalyst stream, and then returning said catalyst to the top of the tubular downflow reactor;
wherein the catalyst of step (a) is accelerated prior to the feed introduction point and is at a temperature of from about 1300° F. to about 1800° F. and is selected from the group consisting of a metal from the transition metal group, a metal oxide from the transition metal group, an alkali compound, a tin oxide, a lead oxide and combinations of the foregoing, and wherein said catalyst comprises particles of from about 20 to about 500 microns in diameter, having a surface area of from about 20 to about 450 m$^2$/g, and wherein there is no input of heat by indirect means.

27. A process for producing a mixture of olefins, comprising:
   (a) introducing a moderate activity catalyst to the top of a tubular downflow reactor to produce a fluidized catalyst stream;
   (b) introducing a feed stream comprising a paraffin having five or fewer carbon atoms into the catalyst stream at a feed introduction point;
   (c) mixing the catalyst stream and the feed stream in a mixing zone to produce a mixed stream;
   (d) passing the mixed stream downward through a reaction zone at a temperature of from about 1330° F. to about 1600° F. and a pressure of from about 10 to about 100 psig to produce an effluent comprising olefins; and
   (e) passing the effluent through a separator to separate the catalyst from the effluent, thereby producing a separated catalyst stream and a clean effluent stream;
wherein the kinetic residence time of said process is from about 0.25 to about 2.0 seconds.

28. A process as defined in claim 27, wherein said process further comprises a step of:
   (f) quenching the clean effluent stream with a quench medium.

29. A process as defined in claim 27, wherein said process further comprises a step of:
   (g) regenerating and reheating the catalyst of said separated catalyst stream, and then returning said catalyst to the top of the tubular downflow reactor.

30. A process as defined in claim 27, wherein the catalyst of step (a) is at a temperature of from about 1300° F. to about 1800° F., and the weight ratio of catalyst to feed in the mixed stream of step (c) is from about 5 to about 100.

31. A process as defined in claim 27, wherein said catalyst of step (a) is accelerated prior to the feed introduction point.

32. A process as defined in claim 27, wherein said feed introduction point of step (b) is in the mixing zone of step (c).

33. The process as defined in claim 27, wherein said catalyst is selected from the group consisting of a metal from the transition metal group, a metal oxide from the transition metal group, an alkali compound, a tin oxide, a lead oxide and combinations of the foregoing.

34. The process as defined in claim 33, wherein said catalyst is selected from the group consisting of iron, iron oxide, nickel, nickel oxide, palladium, palladium oxide, platinum, platinum oxide, vanadium, vanadium oxide, chromium, chromium oxide, manganese, manganese oxide, potassium oxide, and combinations of the foregoing.

35. A process as defined in claim 33, wherein said catalyst is supported upon an inert carrier, and said inert carrier is selected from the group consisting of aluminum oxide, kaolin, amorphous clay, and combinations of the foregoing.

36. A process as defined in claim 33, wherein said catalyst further comprises an aluminosilicate zeolite.

37. A process as defined in claim 33, wherein said catalyst comprises particles from about 20 to about 500 microns in diameter, and have a surface area of from about 20 to about 450 m$^2$/g.

38. A process as defined in claim 27, wherein there is no input of heat by indirect means.

39. A process as defined in claim 27, further comprising the steps of:
   (f) quenching the clean effluent stream with a quench medium; and
   (g) regenerating and reheating the catalyst of said separated catalyst stream, and then returning said catalyst to the top of the tubular downflow reactor;
wherein the catalyst of step (a) is accelerated prior to the feed introduction point and is at a temperature of from about 1300° F. to about 1800° F. and is selected from the group consisting of a metal from the transition metal group, a metal oxide from the transition metal group, an alkali compound, a tin oxide, a lead oxide and combinations of the foregoing, and wherein said catalyst comprises particles of from about 20 to about 500 microns in diameter, having a surface area of from about 20 to about 450 m$^2$/g, and wherein there is no input of heat by indirect means.

* * * * *

UNITED STATES PATENT AND TRADEMARK OFFICE
CERTIFICATE OF CORRECTION

PATENT NO. : 5,254,788
DATED : October 19, 1993
INVENTOR(S) : Robert J. Gartside and Axel R. Johnson It is certified that error appears in the above-identified patent and that said Letters Patent is hereby corrected as shown below:

In Claim 8, column 19, line 32, after the word "consisting", insert --of iron, iron--.

Signed and Sealed this

Sixteenth Day of May, 1995

Attest:

BRUCE LEHMAN

Attesting Officer

Commissioner of Patents and Trademarks